United States Patent [19]

Ziegel

[11] 4,379,510
[45] Apr. 12, 1983

[54] METHOD AND APPARATUS FOR SORTING STONES

[75] Inventor: Douglas H. Ziegel, Indianapolis, Ind.

[73] Assignee: RCA Corporation, New York, N.Y.

[21] Appl. No.: 249,730

[22] Filed: Mar. 31, 1981

[51] Int. Cl.³ .................. B07C 5/00; G01N 21/00
[52] U.S. Cl. .................... 209/643; 209/703; 209/706; 209/942; 209/905; 356/30
[58] Field of Search .............. 209/942, 905, 702, 703, 209/643, 614, 577, 587, 588, 706; 356/30, 31; 221/211; 414/416, 737

[56] References Cited

U.S. PATENT DOCUMENTS

| | | | |
|---|---|---|---|
| 2,338,400 | 1/1944 | Bogue | 209/706 X |
| 2,354,628 | 7/1944 | Whitesell | 209/3.1 X |
| 3,253,719 | 5/1966 | Povlacs et al. | 414/737 |
| 3,730,342 | 5/1973 | Egan et al. | 209/942 |

Primary Examiner—Allen N. Knowles
Attorney, Agent, or Firm—Birgit E. Morris; Donald S. Cohen; Thomas H. Magee

[57] ABSTRACT

An apparatus for sorting stones contained within a supply reservoir by viewing the stones individually through a microscope includes a pick-up tube having a first opening disposed at one end thereof, the first opening adapted to form a substantially airtight seal with one of the stones. A vacuum source is connected to a second opening disposed at the other end of the pick-up tube, the second opening being in communication with the first opening. The apparatus further includes support apparatus connected to the other end of the pick-up tube for moving the one end of the tube between a first position disposed at a transfer location whereat the one end is exposed to the stones within the supply reservoir, and a second position outside the reservoir whereat the one end is positioned exactly within the field of view of an objective of the microscope such that a stone held adjacent the first opening is disposed precisely at the focal length of the microscope objective.

8 Claims, 3 Drawing Figures

METHOD AND APPARATUS FOR SORTING STONES

This invention relates to a method and apparatus for sorting synthetic diamond stones by viewing the stones individually through a microscope.

BACKGROUND OF THE INVENTION

Information playback systems frequently utilize a stylus for reading signals from the surface of an information record, typically a plastic disc, that contains stored video and audio information. In some systems, the information record has a fine spiral groove to guide the tip of a stylus that contains a thin electrode. In these systems, the stylus tip is made of a material having sufficient hardness to withstand the abrasion caused from tracking the groove. Materials which possess such hardness, such as diamond, generally have a crystallographic structure which presents surfaces exhibiting different qualities depending upon which crystallographic plane the surfaces are oriented along. Making a long-shanked stylus entirely from the same material may become expensive, particularly when the tip material, for example diamond, exceeds the cost of other suitable materials from which the shank can be made.

In order to reduce manufacturing costs, the shank of the stylus may be made from a different material which is less expensive than the crystallographic tip material. For example, a small diamond stone may be mounted at the end of a relatively long metallic shank, such as a cylindrical titanium rod. The diamond stone utilized may be a synthetic diamond stone which is less expensive to obtain than a natural diamond stone. The synthetic stone is grown spontaneously in a high-pressure apparatus, containing a metal-carbon system, upon melting of the metal which is in mechanical contact with the graphite. The synthetic diamond stone has a plurality of facets oriented along the {100} family of planes and a plurality of facets oriented along the {111} family of planes. The stone typically comprises an extremely small cubo-octahedron stone having six {100} facets and eight {111} facets, with an average facet-to-facet thickness of approximately 300 micrometers. In actual samples, the facets, along a specific family of planes, are shaped differently and have different surface area sizes, some of which are not desirable for use in stylus tip fabrication. Also, some of the synthetic stones have surface defects which can be discovered by visual examination under a microscope. The present invention provides a novel method and apparatus for sorting synthetic diamond stones in order to determine which of the stones are to be utilized in fabricating metallic-shanked styli.

SUMMARY OF THE INVENTION

The present invention comprises an apparatus for sorting stones contained within a supply reservoir by viewing the stones individually through a microscope. The apparatus includes a pick-up tube having a first opening disposed at one end thereof, the first opening adapted to form a substantially airtight seal with one of the stones. A vacuum source is connected to a second opening disposed at the other end of the pick-up tube, the second opening being in communication with the first opening. The apparatus further includes support means connected to the other end of the pick-up tube for moving the one end of the tube between a first position disposed at a transfer location whereat the one end is exposed to the stones within the supply reservoir; and a second position outside the reservoir whereat the one end is positioned exactly within the field of view of an objective of the microscope such that a stone held adjacent the first opening is disposed precisely at the focal length of the microscope objective.

DETAILED DESCRIPTION OF THE PREFERRED EMBODIMENT

Figure 1:
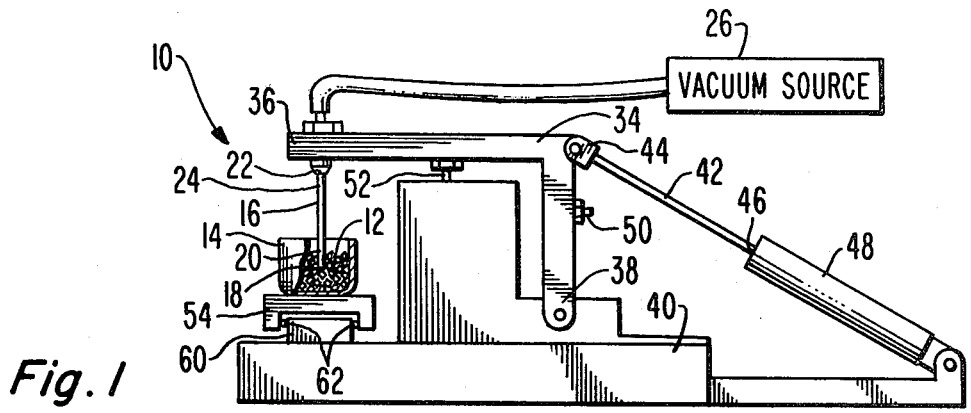
FIG. 1 is an elevation view showing a preferred embodiment of the novel stone sorting apparatus in a first position, with a section of a supply reservoir broken away.

In FIG. 1 of the drawing, there is shown one embodiment of an apparatus 10 for sorting stones 12 contained within a supply reservoir 14. The apparatus 10 comprises a pick-up tube 16 having a first opening 18 disposed at one end 20 thereof. The first opening 18 is adapted to form a substantially airtight seal with one of the stones 12, so as to allow the one end 20 to hold only one of the stones 12 adjacent the first opening 18 when a vacuum is applied thereto. The stones 12 comprise synthetic diamond stones having the shape of a cubo-octahedron with a facet-to-facet thickness of about 300 micrometers. Since the stones 12 are multifaceted, there will be some gaps between the opening 18 and the edge of a stone 12 being held thereto; it is not necessary that the seal therebetween be airtight, but only sufficient to hold the stone 12 adjacent the one end 20. In the present embodiment, the pick-up tube 16 comprises a thin hypodermic needle, and the first opening 18 has a diameter of about 200 micrometers.

A second opening 22 is disposed at the other end 24 of the pick-up tube 16 and is connected to a vacuum source 26. The second opening 22 is in communication with the first opening 28 via an internal conduit, so as to allow a vacuum to be applied to the first opening 18. The vacuum source 26 should be sufficient to hold one of the stones 12 adjacent the first opening 18.

Figure 2:
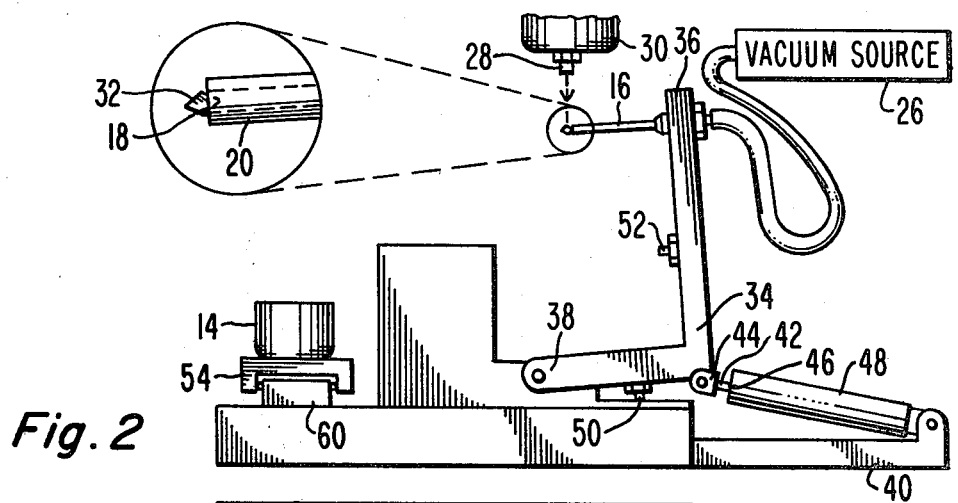
FIG. 2 is an elevation view of the novel stone sorting apparatus in a second position.

Support means is connected to the other end 24 of the pick-up tube 16 for moving the one end 20 of the tube 16 between a first position disposed at a transfer location whereat the one end 20 is exposed to the stones 12 within the supply reservoir 14, and a second position outside the reservoir 14. At the second position, the one end 20 is positioned exactly within the field of view of an objective 28 of a microscope 30, such that a sample stone 32 held adjacent the first opening 18 is disposed precisely at the focal length of the microscope objective 28, as shown in FIG. 2. In the present embodiment, the support means comprises a rotating arm 34 having a sweeping end 36 connected to the other end 24 of the pick-up tube 16, and a pivot end 38 rotatably supported by a platform 40. The arm 34 is substantially "L-shaped" with one leg of the "L" comprising the sweeping end 36, and the other leg of the "L" comprising the pivot end 38. The arm 34 is connected to means for rotating the arm 34 about the pivot end 38. The rotating means may comprise a piston rod 42 having one end 44 connected to the arm 34 at a location away from the pivot end 38 near the vertex of the "L", and having the other end 46 connected to a piston of an air cylinder 48 supported by the platform 40, as shown in FIGS. 1 and 2. The air cylinder 48 is connected to an external air source (not shown) adapted to move the piston rod 42 back and forth. The rotating arm 34 may have adjustable "up" and "down" stops 50 and 52 connected, respectively, to the legs of the L-shaped arm 34 for contacting the platform 40 and assisting in the precise positioning of the one end 20 of the pick-up tube 16. The position of the platform 40 is always fixed in relation to the position of the microscope 30.

Figure 3:
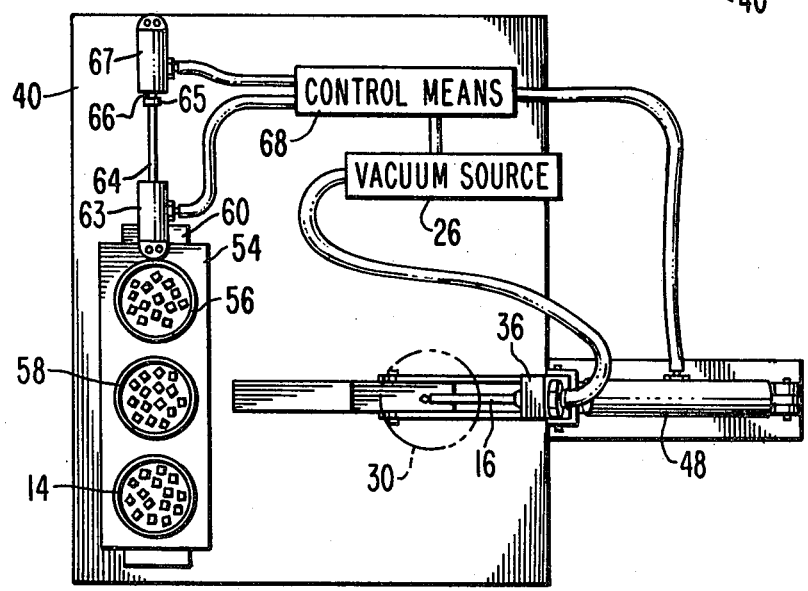
FIG. 3 is a plan view of the novel stone sorting apparatus in the second position.

The apparatus 10 may further comprise a sliding tray 54 adapted to support the supply reservoir 14 along with a reject reservoir 56 and an accept reservoir 58, as illustrated in FIG. 3. The tray 54 is attached to the platform by means for sliding the tray 54 back and forth to allow each of the reservoirs 14, 56, and 58 to be positioned at the transfer location, which is the location wherein the one end 20 of the pick-up tube 16, while at the first position, has access thereto. In the present embodiment, the sliding means comprises a guide rail 60 having a ball slide 62 for supporting the tray 54 and facilitating its movement along the guide rail 60. The tray 54 is connected to a first air cylinder 63 which has its piston 64 connected in series, by a coupling 65, to the piston 66 of a second air cylinder 67 which is supported by the platform 40. By having the piston stroke of the second cylinder 67 be twice that of the first cylinder 63, it is possible to provide four positions for the tray 54, although only three are needed in the present embodiment. When both the first and the second cylinders 63 and 67 are retracted, the supply reservoir 14 is positioned at the transfer location. When the first cylinder 63 is extended and the second cylinder 67 is retracted, the accept reservoir 58 is positioned at the transfer location, as illustrated in FIG. 3. The reject reservoir 56 is positioned at the transfer location when the first cylinder 63 is retracted and the second cylinder 67 is extended. The possibility of a fourth position is available when both the first and the second cylinders 63 and 67 are extended. The first and the second cylinders 63 and 67 are operated by control means 68 for automatically indexing each of the reservoirs 14, 56, and 58 at the transfer location. In the present example, the control means 68 also operates the air cylinder 48 used for rotating the arm 34, and controls the vacuum source 26.

The present method of sorting the stones 12 contained within the supply reservoir 14 comprises the first step of placing the one end 20 of the pick-up tube 16 at the first position, where the one end 20 is exposed to the stones 12 within the supply reservoir 14. The vacuum source 26 is applied to the second opening 22, whereby the sample stone 32 is firmly held adjacent the first opening 18.

The one end 20 of the pick-up tube 16 is then moved from the first position to the second position outside the reservoir 14, whereat the one end 20 is positioned exactly within the field of view of the microscope objective 28. Since the sample stone 32 is now disposed precisely at the focal length of the microscope objective 28, an operator may easily determine whether the sample stone 32 is to be rejected or accepted by visually observing the sample stone 32 through the microscope 30.

After making this determination, the operator replaces the supply reservoir 14 at the transfer location with either the reject reservoir 56 or the accept reservoir 58 depending, respectively, upon whether the sample stone 32 is to be rejected or accepted. In the present example, this replacing step is performed by an operator-initiated input signal from the control means 68 which causes the tray 54 to slide along the guide rail 60 until the appropriate reservoir 56 or 58 is positioned at the transfer location. The one end 20 of the pick-up tube 16 is now returned to the first position, and the vacuum source 26 is removed in order to release the sample stone 32 into the reservoir 56 or 58 positioned at the transfer location. Depending upon the configuration of the first opening 18, it may be desirable to use a positive pressure through the pick-up tube 16 to insure release of the sample stone 32. The pick-up tube 16 is then returned to the second position, and the above-described sequence of steps is repeated.

The present invention provides an efficient handling apparatus by which to visually inspect a large number of synthetic diamond stones in rapid succession. It is emphasized that the synthetic stones are extremely small, having a typical facet-to-facet thickness of about 300 micrometers. The small supply reservoir 14 will contain several thousand synthetic stones, each needing to be visually examined prior to being further processed. Since the synthetic stone is so small, it would be time consuming to have to not only manually handle each stone but also to manually locate the stone each time in the field of view of the microscope 30. The present invention provides an efficient apparatus and method which allows each individual stone to be automatically placed precisely in the field of view of the microscope 30, ready for visual examination by the operator. In actual operation, the control means automatically places the pick-up tube 16 in the first position to pickup the sample stone 32, and moves to the second position to await the input signal from the operator, who then visually examines the stone 32 through the microscope 30. The operator then pushes either a reject button or an accept button which then initiates the above-described automatic indexing steps. In rapid succession, the sample stone 32 is released into the appropriate reservoir 56 or 58, and the next stone is picked up and brought to the second position, awaiting the next input signal from the operator. By using the present apparatus 10, the operator in effect has to only look through the microscope and then press either the reject or accept button, thereby achieving the rapid sorting of a large number of stones.

What is claimed is:

1. An apparatus for sorting stones contained within a supply reservoir by viewing said stones individually through a microscope comprising:

a pick-up tube having a first opening disposed at one end thereof, said first opening adapted to form a substantially airtight seal with one of said stones, a vacuum source connected to a second opening disposed at the other end of said pick-up tube, said second opening being in communication with said first opening, support means supported by a platform and connected to the other end of said pick-up tube for moving the one end of said tube between a first position disposed at a transfer location whereat said one end is exposed to the stones within the supply reservoir, and a second position outside said reservoir whereat said one end is positioned exactly within the field of view of an objective of said microscope such that a stone held adjacent said first opening is disposed precisely at the focal length of said microscope objective, and a sliding tray adapted to support said supply reservoir along with a reject reservoir and an accept reservoir, said tray attached to said platform by means for sliding said tray back and forth to allow each of said reservoirs to be positioned at said transfer location wherein the one end of said pick-up tube, while at said first position, has access thereto.

2. An apparatus as defined in claim 1 wherein said support means for moving the one end of said pick-up tube comprises a rotating arm having a sweeping end connected to the other end of said pick-up tube and a pivot end rotatably supported by said platform, said arm connected to means for rotating said arm about said pivot end.

3. An apparatus as defined in claim 2 wherein said rotating means comprises a piston rod having one end connected to said arm at a location away from said pivot end and having the other end connected to a piston of an air cylinder supported by said platform.

4. An apparatus as defined in claim 2 wherein said sliding means comprises a guide rail having a ball slide for supporting said tray, said tray being connected to a pair of air cylinders connected in series and operated by control means for automatically indexing each of said reservoirs at said transfer location.

5. An apparatus as defined in claim 2 wherein said pick-up tube comprises a needle, and wherein the diameter of said opening is about 200 micrometers.

6. A method of sorting stones within a supply reservoir by viewing said stones individually through a microscope comprising the steps of:

placing one end of a pick-up tube at a first position disposed at a transfer location whereat said one end is exposed to the stones within said supply reservoir, said pick-up tube having a first opening disposed at said one end, said first opening adapted to form a substantially airtight seal with one of said stones, applying a source of vacuum to a second opening disposed at the other end of said pick-up tube, said second opening being in communication with said first opening, whereby a sample stone is held adjacent said first opening, moving the one end of said pick-up tube from said first position to a second position outside said supply reservoir whereat said one end is positioned exactly within the field of view of an objective of said microscope such that said sample stone is disposed precisely at the focal length of said microscope objective, determining whether said sample stone is to be rejected or accepted by visually observing the sample stone through said microscope when the one end of said pick-up tube is disposed at said second position, replacing said supply reservoir at said transfer location with either a reject reservoir or an accept reservoir depending, respectively, upon whether said sample stone is to be rejected or accepted, returning the one end of said pick-up tube to said first position, and removing said source of vacuum in order to release said sample stone from said first opening, whereby the sample stone is deposited in the reservoir positioned at said transfer location.

7. A method as recited in claim 6 wherein said replacing step is performed by sliding a tray back and forth along a guide rail in a manner whereby each of said reservoirs, supported by said tray, may be automatically indexed at said transfer location.

8. A method as recited in claim 6 wherein said stones comprise synthetic diamond stones having the shape of a cubo-octahedron with a facet-to-facet thickness of about 300 micrometers.

* * * * *